US012582401B2

(12) United States Patent
     Eisinger

(10) Patent No.: US 12,582,401 B2
(45) Date of Patent: Mar. 24, 2026

(54) ADAPTER ASSEMBLY WITH CONSTANT VELOCITY JOINTS

(71) Applicant: Covidien LP, Mansfield, MA (US)

(72) Inventor: Joseph T. Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/864,966

(22) PCT Filed: May 8, 2023

(86) PCT No.: PCT/IB2023/054756
     § 371 (c)(1),
     (2) Date: Nov. 12, 2024

(87) PCT Pub. No.: WO2023/223142
     PCT Pub. Date: Nov. 23, 2023

(65) Prior Publication Data
     US 2025/0302478 A1     Oct. 2, 2025

Related U.S. Application Data

(60) Provisional application No. 63/342,428, filed on May 16, 2022.

(51) Int. Cl.
     *F16D 3/30*        (2006.01)
     *A61B 17/115*      (2006.01)
     *A61B 17/00*       (2006.01)
(52) U.S. Cl.
     CPC ............. *A61B 17/1155* (2013.01); *F16D 3/30* (2013.01); *A61B 2017/00473* (2013.01); *A61B 2017/00486* (2013.01)

(58) Field of Classification Search
     CPC .............................. A61B 17/1155; F16D 3/30
     See application file for complete search history.

(56) References Cited

U.S. PATENT DOCUMENTS

| | | | |
|---|---|---|---|
| 4,362,520 A | 12/1982 | Perry | |
| 4,840,601 A | 6/1989 | Denman | |
| 2010/0031369 A1 | 2/2010 | Grummt | |
| 2010/0313692 A1 | 12/2010 | Wenzel | |
| 2016/0106406 A1* | 4/2016 | Cabrera | ............. A61B 17/1155 |
| | | | 606/1 |
| 2020/0222149 A1* | 7/2020 | Valentine | ............... A61B 17/00 |
| 2021/0086376 A1 | 3/2021 | Eijkelkamp et al. | |
| 2021/0177423 A1* | 6/2021 | Mozdzierz | ............. A61B 90/98 |

(Continued)

OTHER PUBLICATIONS

PCT/IB2023/054756, International Search Report and Written Opinion, mailed Jul. 20, 2023, 13pages.

*Primary Examiner* — Nathaniel C Chukwurah

(57) ABSTRACT

A drive assembly for an adapter assembly of a surgical device includes an input shaft, a middle shaft, and an output shaft. The input shaft includes a proximal portion configured for operable engagement with a drive member of a handle assembly and a distal portion including a first castellated portion. The middle shaft includes a proximal portion having a first lobed portion in operable engagement with the first castellated portion of the input shaft, and a distal portion having a second lobed portion. The output shaft includes a proximal portion having a second castellated portion in operable engagement with the second lobed portion.

18 Claims, 7 Drawing Sheets

(56) References Cited

U.S. PATENT DOCUMENTS

| | | | | | |
|---|---|---|---|---|---|
| 2021/0244875 | A1* | 8/2021 | Eisinger | .............. | A61M 3/0279 |
| 2021/0315660 | A1* | 10/2021 | Williams | ......... | A61B 17/00234 |
| 2021/0315663 | A1* | 10/2021 | Williams | ............... | A61B 90/70 |

* cited by examiner

ADAPTER ASSEMBLY WITH CONSTANT VELOCITY JOINTS

CROSS-REFERENCE TO RELATED APPLICATIONS

This application is a National Stage Application of PCT/IB2023/054756 filed May 8, 2023, which claims benefit of and priority to U.S. Provisional Application No. 63/342,428 filed May 16, 2022, and the disclosures of each of the above-identified applications are hereby incorporated by reference in their entirety.

FIELD

The disclosure relates to adapter assemblies of powered surgical devices. More particularly, the disclosure relates to adapter assemblies having a drive assembly with lobed and castellated constant velocity (CV) joints to transfer rotational power through a curved portion of the adapter assembly.

BACKGROUND

Powered surgical devices that include an adapter assembly for connecting an end effector to a handle assembly are known. The adapter assemblies of the powered surgical devices include one or more drive members, e.g., screw, shaft, cable, band, to transfer power from an actuation unit, e.g., a handle assembly, to an attached end effector. Generally, the actuation assemblies are configured to supply rotational power to the adapter assemblies, and the adapter assemblies are configured to transform the rotational power into a push/pull force that is transferred to the end effector. Alternatively, the adapter assemblies may be configured to transfer the rotational power to the attached end effector as rotational force.

Many adapter assemblies include a curved portion to facilitate positioning of an attached end effector within a patient. A drive assembly extending through the curved portion of the adapter assembly may include a flexible drive shaft to accommodate the curve. Alternatively, the drive assembly may use multiple rigid shafts connected to each other at constant velocity (CV) joints. Traditional CV joints used in adapter assemblies of powered surgical devices include a first shaft having a ball member formed on distal end portion pinned within a slot defined in a U-shaped socket formed on proximal end portion of a second shaft. Traditional CV joints are complex and may be cost prohibitive.

Therefore, it would be beneficial to have a drive assembly for an adapter assembly that includes one or more improved CV joints.

SUMMARY

A drive assembly for an adapter assembly of a surgical device includes an input shaft, a middle shaft, and an output shaft. The input shaft has a proximal portion and a distal portion. The proximal portion of the input shaft is configured for operable engagement with a drive member of a handle assembly and the distal portion of the input shaft includes a first castellated portion. The middle shaft has a proximal portion and a distal portion. The proximal portion of the middle shaft includes a first lobed portion in operable engagement with the first castellated portion of the input shaft, and the distal portion of the middle shaft includes a second lobed portion. The output shaft has a proximal portion and a distal portion. The proximal portion of the output shaft includes a second castellated portion in operable engagement with the second lobed portion.

In aspects of the disclosure, the first lobed portion and the second lobed portion each include three lobe members. The first castellated portion and the second castellated portion may each include three flange members. The first castellated portion and the second castellated portion may define three cutouts. The cutouts of the first castellated portion correspond in number to the number of lobe members of the first lobed portion, and the cutouts of the second castellated portion correspond in number to the number of lobe members of the second lobed portion.

In certain aspects of the disclosure, each lobe member of the three lobe members of the first and second lobed portions includes a semi-cylindrical portion and a waist portion. Each of the first lobed portion and the second lobed portion may define three recesses. The waist portions and the three recesses of the three lobe members of the first lobed portion may accommodate pivoting of the middle shaft relative to the input shaft. The waist portion and the three recesses of the three lobe members of the second lobed portion may accommodate pivoting of the output shaft relative to the middle shaft. The distal portion of the output shaft may include a drive screw.

An adapter assembly for connecting a handle assembly to an end effector includes a coupling assembly, a straight portion, a curved portion, and a drive assembly. The coupling assembly is configured for operable connection with a handle assembly. The straight portion is secured to the coupling assembly. The curved portion extends from the straight portion. The drive assembly extends from the handle assembly through the curved portion. The drive assembly includes an input shaft, a middle shaft, and an output shaft. The input shaft has a proximal portion and a distal portion. The proximal portion of the input shaft is configured for operable engagement with a drive member of a handle assembly and the distal portion of the input shaft includes a first castellated portion. The middle shaft has a proximal portion and a distal portion. The proximal portion of the middle shaft includes a first lobed portion in operable engagement with the first castellated portion of the input shaft, and the distal portion of the middle shaft includes a second lobed portion. The output shaft has a proximal portion and a distal portion. The proximal portion of the output shaft includes a second castellated portion in operable engagement with the second lobed portion.

In aspects of the disclosure, the first lobed portion and the second lobed portion of the middle shaft of the drive assembly both include three lobe members. The first castellated portion and the second castellated portion of the input shaft and output shaft, respectively, may each include three flange members. The first castellated portion and the second castellated portion may define three cutouts. The cutouts of the first castellated portion correspond in number to the number of lobe members of the first lobed portion, and the cutouts of the second castellated portion correspond in number to the number of lobe members of the second lobed portion.

In certain aspects of the disclosure, each lobe member of the three lobe members of the first and second lobed portions includes a semi-cylindrical portion and a waist portion. Each of the first lobed portion and the second lobed portion may define three recesses. The waist portions and the three recesses of the three lobe members of the first lobed portion may accommodate pivoting of the middle shaft relative to the input shaft. The waist portion and the three recesses of the three lobe members of the second lobed portion may accommodate pivoting of the output shaft relative to the middle shaft. The distal portion of the output shaft may include a drive screw.

A surgical device includes a handle assembly, an adapter assembly, an end effector, and a drive assembly. The handle assembly includes a drive member. The adapter assembly is secured to the handle assembly. The end effector is secured to the adapter assembly. The drive assembly extends from the handle assembly and is positioned within the adapter assembly. The drive assembly includes an input shaft, a middle shaft, and an output shaft. The input shaft has a proximal portion and a distal portion. The proximal portion of the input shaft is configured for operable engagement with a drive member of a handle assembly and the distal portion of the input shaft includes a first castellated portion. The middle shaft has a proximal portion and a distal portion. The proximal portion of the middle shaft includes a first lobed portion in operable engagement with the first castellated portion of the input shaft, and the distal portion of the middle shaft includes a second lobed portion. The output shaft has a proximal portion and a distal portion. The proximal portion of the output shaft includes a second castellated portion in operable engagement with the second lobed portion.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspects given below, explain the principles of the disclosure, wherein.

DETAILED DESCRIPTION

Figure 1:
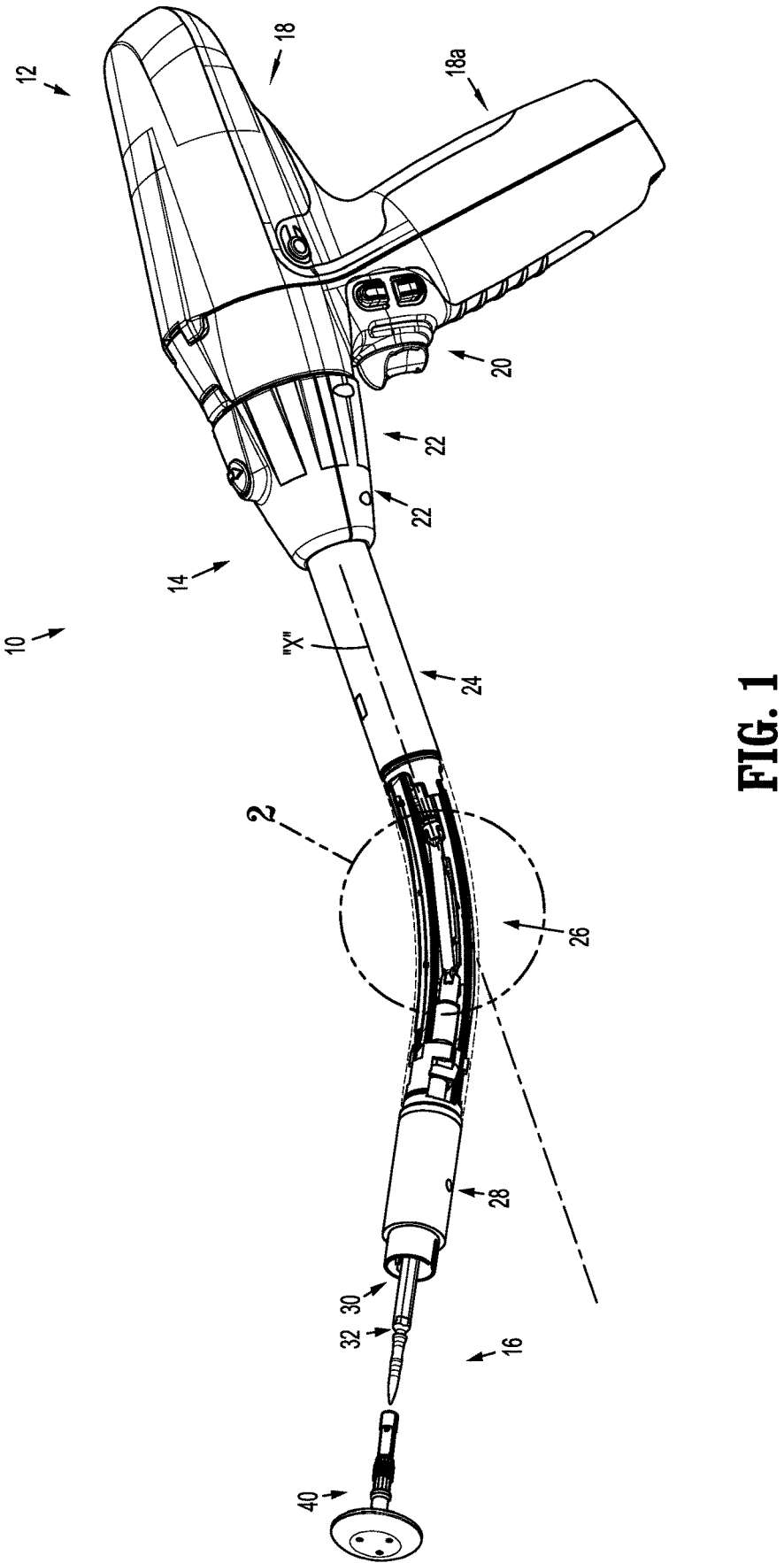
FIG. 1 is a side perspective view of a surgical stapling device including an adapter assembly with a drive assembly according to aspects of the disclosure.

The disclosed powered surgical device and drive assembly will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the stapling device in its customary manner, while the term "distal" is used generally to refer to that portion of the device that is farther from the clinician during use of the stapling device in its customary manner. In addition, the term "clinician" is used generally to refer to medical personnel including doctors, nurses, and support personnel. Further, directional terms such as front, rear, upper, lower, top, bottom, and similar terms are used to assist in understanding the description and are not intended to limit the disclosure.

The disclosed powered surgical device includes a drive assembly that transfers rotational power from a handle assembly of the powered surgical device to an end effector of the powered surgical device. The adapter assembly includes a curved portion to facilitate positioning of the end effector within a patient. The drive assembly includes first and second constant velocity (CV) joints that accommodate the curvature of the adapter assembly. The CV joints include a middle shaft having lobed proximal and distal portions, an input shaft having a castellated portion engaged with the lobed proximal portion of the middle shaft, and an output shaft having a castellated portion engaged with the lobed distal portion of the output shaft. As will become apparent from the below description, the disclosed CV joints are significantly stronger, less complex, and less costly than traditional CV joints.

FIG. 1 illustrates a powered surgical device according to aspects of the disclosure shown generally as stapling device 10. The stapling device 10 will only be described to the extent necessary to fully disclose the aspects of the disclosure. For a detailed description of exemplary adapter assemblies, please refer to U.S. Pat. No. 10,226,254 ("the '254 patent").

The stapling device 10 includes handle assembly 12, an adapter assembly 14, and an end effector 16. The handle assembly 12 includes a body 18 that defines a hand grip 18*a* and includes a plurality of actuator buttons 20. The actuator buttons 20 control operation of the various functions of the stapling device 10 including clamping, firing, and cutting of tissue. Although shown to include a handle assembly 12, it is envisioned that the adapter assembly 14 may be configured as a component in a robotic system (not shown).

The adapter assembly 14 of the stapling device 10 includes a coupling assembly 22, a straight portion 24 extending from the coupling assembly 22, a curved portion 26 extending from the straight portion 24, and a connector assembly 28 secured to a distal portion of the curved portion 26. The coupling assembly 22 includes a rotation knob 22*a* for rotating the end effector 16 about a longitudinal axis "X" of the straight portion 24. The connector portion 28 of the adapter assembly 14 is configured to releasably receive a circular stapler reload or loading unit (not shown). A trocar assembly 30 is positioned within the connector assembly 28 and includes a trocar member 32 that extends from the connector portion 28. The trocar member 32 of the trocar assembly 30 is configured to releasably receive an anvil assembly 40 and is selectively movable between advanced and retracted positions to position the anvil assembly 40 relative to a circular stapler reload (not shown) secured to the connector assembly 28 of the adapter assembly 14.

Although shown and described with reference to stapling device 10, aspects of the disclosure may be modified for use with any surgical device (powered or manual) having a rotatable drive shaft. Aspects of the disclosure may also be incorporated into a robotic system having a rotating drive shaft.

Figure 2:
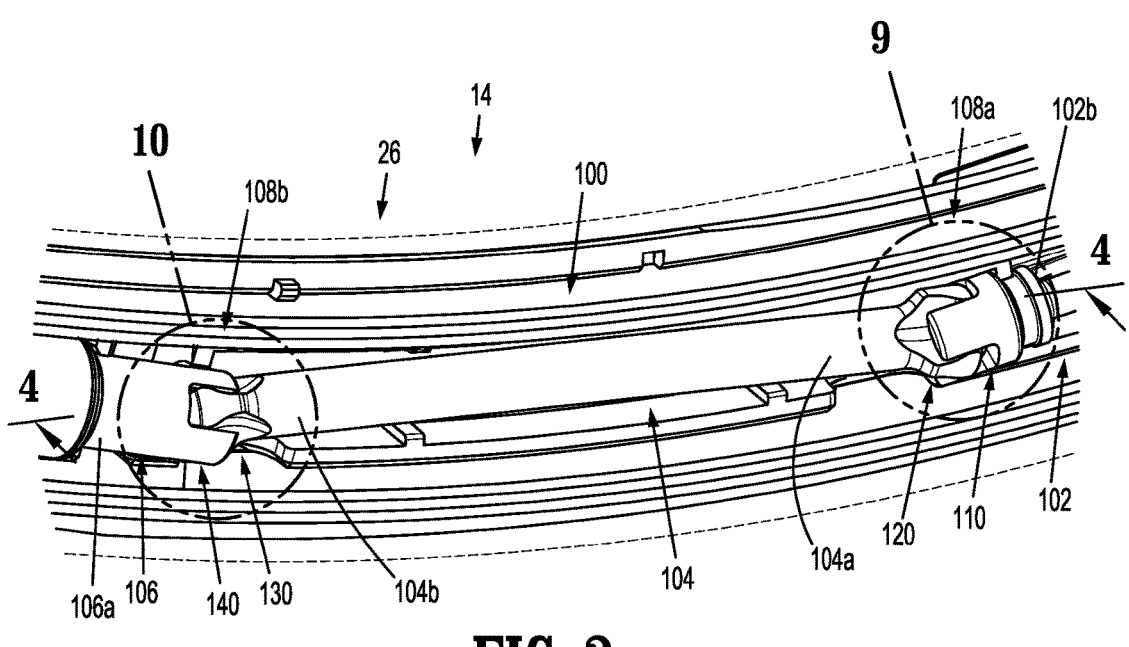
FIG. 2 is an enlarged view of the indicated area of detail shown in FIG. 1.
Figure 3:
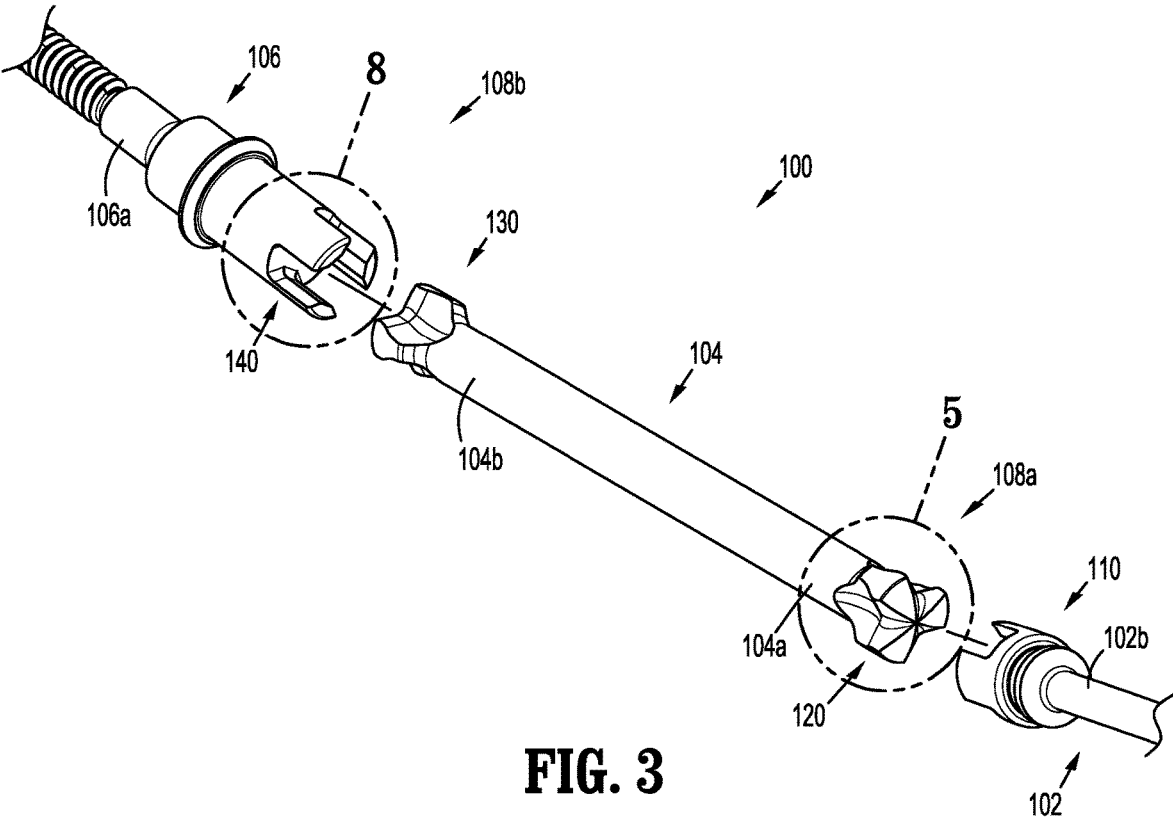
FIG. 3 is a perspective view of a portion of the drive assembly shown in FIG. 1.

FIGS. 2 and 3 illustrate a drive assembly 100 of the adapter assembly 14 of the stapling device 10 (FIG. 1). The drive assembly 100 is configured to operably connect a rotating drive member (not shown) of the handle assembly 12 with the trocar assembly 30 of the end effector 16. The drive assembly 100 includes an input shaft 102, a middle or connector shaft 104, and an output shaft or drive screw 106. The input shaft 102 of the drive assembly 100 extends through the straight portion 24 of the adapter assembly 14 and includes a proximal portion (not shown) in operable connection with the drive member (not shown) of the handle assembly 12, as known in the art. The handle assembly 12 supplies rotational power to the input shaft 102, as detailed in the '254 patent. The output shaft 106 may be a component of the trocar assembly 30 (FIG. 1) or may otherwise operably engage the trocar assembly 30. Rotation of the output shaft 106 in a first direction results in advancement of the trocar member 32 (FIG. 1) relative to the output shaft 106 and rotation of the output shaft 106 in a second direction results in retraction of the trocar assembly 32 relative to the output shaft 106.

The input shaft 102, the middle shaft 104, and the output shaft 106 of the drive assembly 100 may be formed of stainless steel or other material having a high yield strength, e.g., PEEK. It is envisioned that the input shaft 102, the middle shaft 104, and the output shaft 106 may be formed of the same or different materials.

A distal portion 102b of the input shaft 102 of the drive assembly 100 includes a first castellated portion 110. Proximal and distal portions 104a, 104b of the middle shaft 104 include first and second lobed portions 120, 130, respectively. A proximal portion 106a of the output shaft 106 includes a second castellated portion 140. The first castellated portion 110 of the input shaft 102 engages the first lobed portion 120 of the middle shaft 104 to form a first joint 108a. The second castellated connector 140 engages the second lobed connector 130 of the middle shaft 104 to form a second joint 108b.

Figure 4:
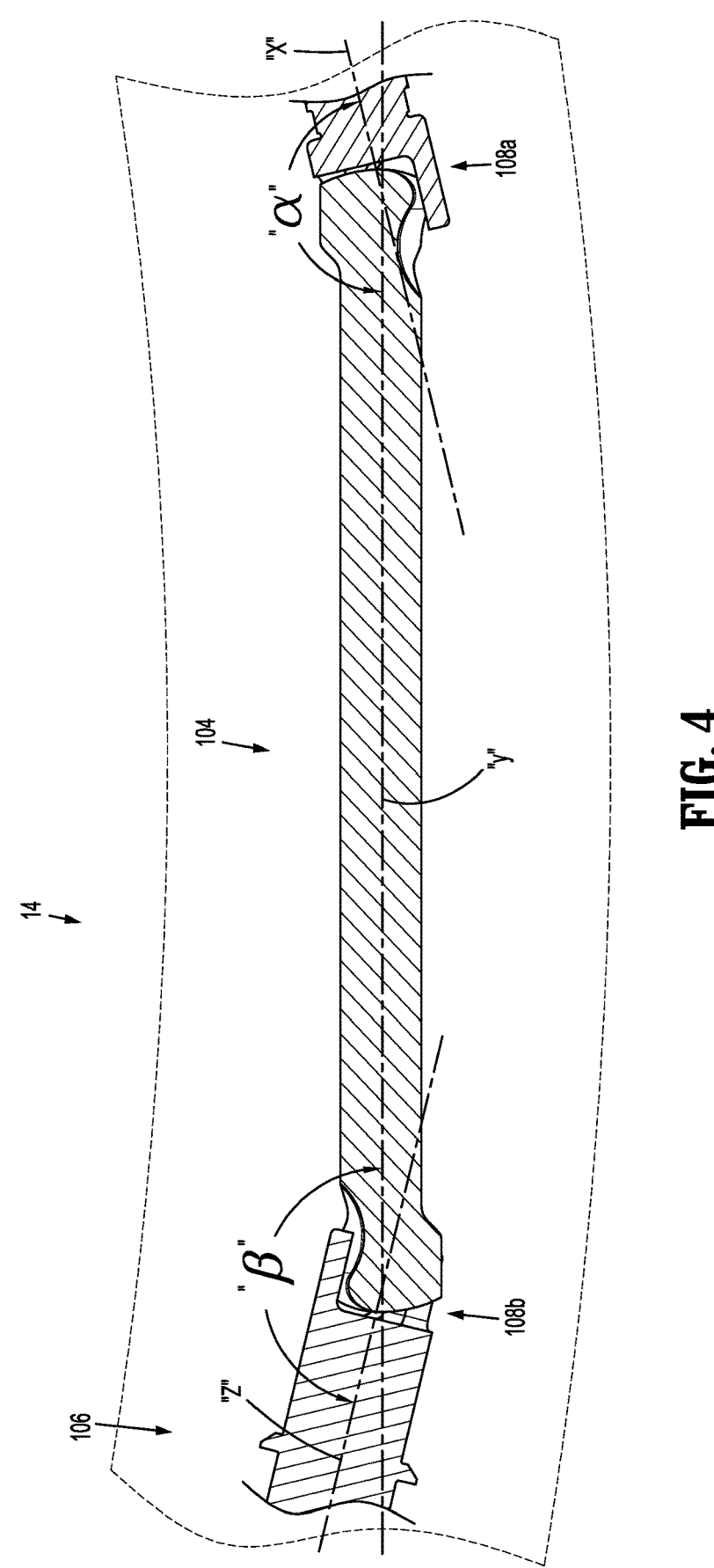
FIG. 4 is a cross-sectional side view taken along line 4-4 shown in FIG. 2.

FIG. 4 illustrates positions of the input shaft 102, the middle shaft 104, and the output shaft 106 relative to each other. As shown, a longitudinal axis "x" of the input shaft 102 is at a first angle "α" relative to a longitudinal axis "y" of the middle shaft 104. The longitudinal axis "y" of the middle shaft 104 is at a second angle "β" relative to a longitudinal axis "z" of the output shaft 106. As will be described in further detail below, the configuration of the first and second joints 108a, 108b is such that the first and second angles "α", "β" may be between 0° and 15°, and may be the same or different.

Although shown as extending through a rigid or semirigid curved portion 26 of the adapter assembly 14, and thus having fixed first and second angles "α", "β", it is envisioned that the drive assembly 100 may extend through a flexible portion (not shown) of an adapter 100. In this manner, the first and second angles "α", "β" are not fixed and the middle shaft 104 may be pivoted away from the longitudinal axis "x" of the input shaft 102 in any direction. Similarly, the output shaft 106 may be pivoted away from the longitudinal axis "y" of the middle shaft 104 in any direction. It is further envisioned that the drive assembly 100 may accommodate flexing of the adapter assembly 14 during operation of the stapling device 10 (FIG. 1).

Figure 5:
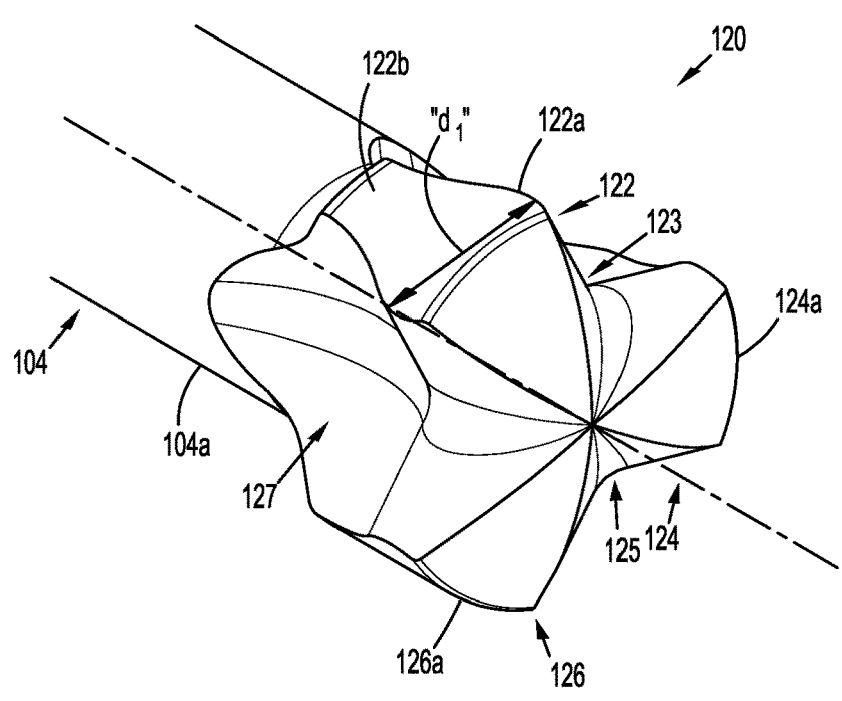
FIG. 5 is an enlarged view of the indicated area of detail shown in FIG. 3.

FIG. 5 illustrates the first lobed portion 120 on the proximal portion 104a of the middle shaft 104 of the drive assembly 100. In aspects of the disclosure, the first lobed portion 120 includes first, second, and third lobe members 122, 124, 126. The first, second, and third lobe members 122, 124, 126 extend radially outward normal to the longitudinal axis "y" of the middle shaft 104 and are equally spaced from each other. As such, an angle between the first, second, and third lobe members 122, 124, 126 and the respective adjacent second, third and first lobe member 124, 126, 122 is one-hundred and twenty degrees (120°). The first lobed portion 120 defines a first recess 123 formed between the first lobe member 122 and the second lobe member 124, a second recess 125 formed between the second lobe member 124 and the third lobe member 126, and a third recess 127 formed between the third lobe member 126 and the first lobe member 122.

Each of the first, second, and third lobe members 122, 124, 126 of the first lobed portion 120 includes a semi-cylindrical section 122a, 124a, 126a, respectively, and a waist section 122b, 124b, 126b, respectively. Each of the semi-cylindrical sections 122a, 124a, 126a of the respective first, second, and third lobe members 122, 124, 126 include a diameter "$d_1$".

Figure 6:
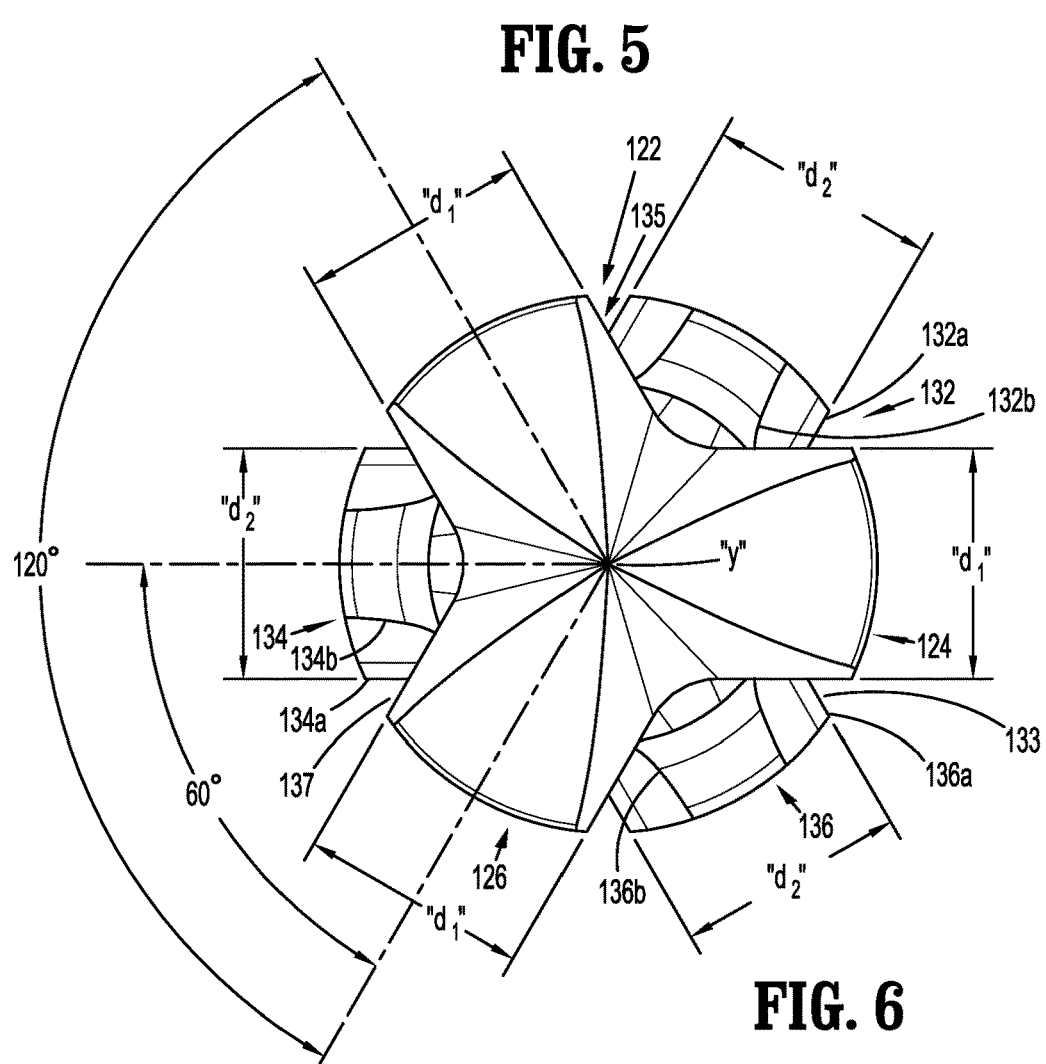
FIG. 6 is a proximal end view of a middle shaft of the drive assembly shown in FIG. 3.

FIG. 6 illustrates an end view of the middle shaft 104 of the drive assembly 100 with the first lobed portion 120 in the foreground and the second lobed portion 130 in the background. The second lobed portion 130 is substantially similar to the first lobed portion 120, and includes first, second, and third lobe members 132, 134, 136, and defines a first recess 133 between the first lobe member 132 and the second lobe member 134, a second recess 135 between the second lobe member 134 and the third lobe member 136, and a third recess 137 between the third lobe member 136 and the first lobe member 132. The first, second, and third lobe members 132, 134, 136 of the second lobed portion 130 are radially offset from the first, second, and third lobe members 122, 124, 126 of the first lobed portion 120 by sixty degrees (60°). In this manner, the rotational force passing through the middle shaft 104 is evenly distributed as the middle shaft 104 is rotated about its longitudinal axis "y" by the input shaft 102 of the drive assembly 100.

Each of the first, second, and third lobe members 132, 134, 136 of the second lobed portion 130 includes a semi-cylindrical section 132a, 134a, 136a, respectively, and a waist section 132b, (FIG. 6) 134b, 136b, respectively. Each of the semi-cylindrical sections 132a, 134a, 136a of the respective first, second, and third lobe members 132, 134, 136 includes a diameter "$d_2$". As shown, the diameters "$d_2$" of the semi-cylindrical sections 132a, 134a, 136a of the second lobed portion 130 are the same as the diameters "$d_1$" of the semi-cylindrical sections 122a, 124a, 126a of the first lobed portion 120. It is envisioned that diameters "$d_2$" of the semi-cylindrical sections 132a, 134a, 136a of the second lobed portion 130 may be different than the diameters "$d_1$" of the semi-cylindrical sections 122a, 124a, 126a of the first lobed portion 120.

Although shown including three lobe members, it is envisioned that the first lobed portion 120 and the second lobed portion 130 may include more than three lobe members. It is also envisioned that the number of lobe members on the first and second lobed portions 120, 130 may be different.

Figure 7:
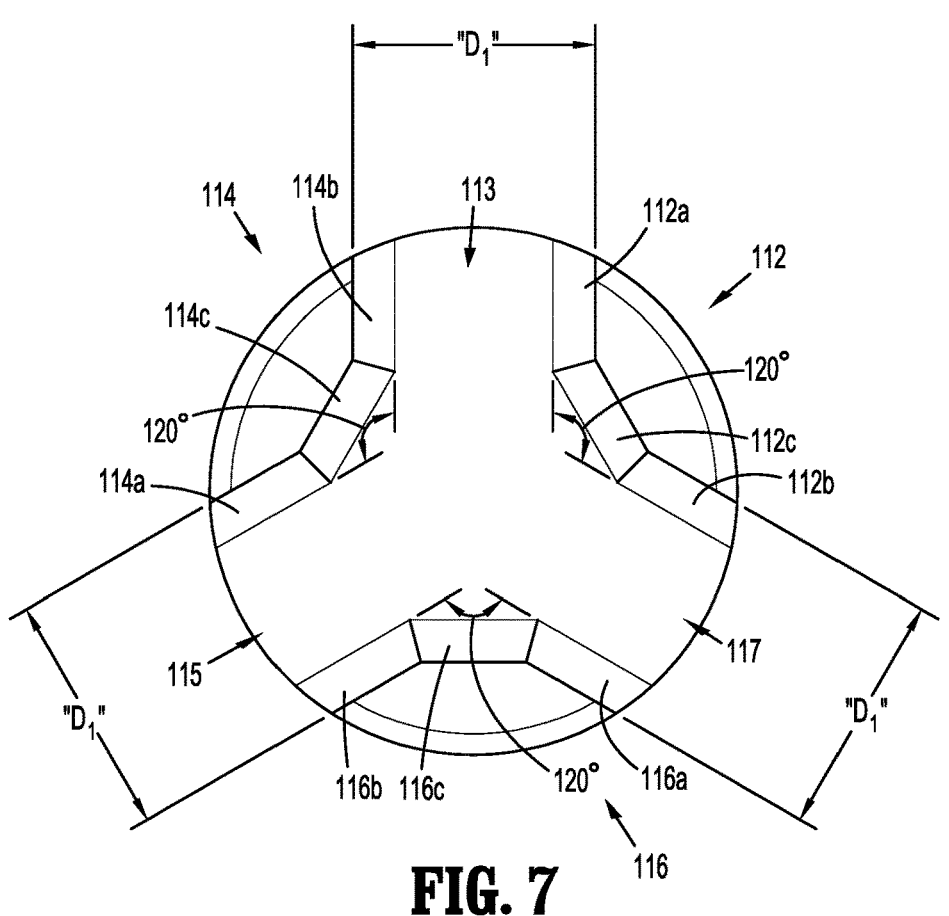
FIG. 7 is a distal end view of an input shaft of the drive assembly shown in FIG. 3.

FIG. 7 illustrates the first castellated portion 110 on the distal portion 102*b* of the input shaft 102 of the drive assembly 100. The first castellated portion 110 includes first, second, and third flange members 112, 114, 116. The number of flange members correspond to the number of lobe members of the first lobed portion 120. Each of the first, second, and third flange members 112, 114, 116 includes a first inner tapered surface 112*a*, 114*a*, 116*a*, respectively, a second inner tapered surface 112*b*, 114*b*, 116*b*, respectively, and a planar surface 112*c*, 114*c*, 116*c*, respectively, extending between the respective first tapered surfaces 112*a*, 114*a*, 116*a*, and the respective second tapered surfaces 112*b*, 114*b*, 116*b*. The planar surfaces 112*c*, 114*c*, 116*c* of the respective first, second, and third flange members 112, 114, 116 define a longitudinal recess 111 configured to receive the first lobed portion 120 on the middle shaft 104 of the drive assembly 100.

Each of the first inner tapered surfaces 112*a*, 114*a*, 116*a* of the respective first, second, and third flange members 112, 114, 116 forms an angle of one-hundred and twenty degrees (120°) relative to the respective second inner tapered surfaces 112*b*, 114*b*, 116*b* of the first, second, and third flange members 112, 114, 116. In this manner, the first inner tapered surface 112*a* of the first flange member 112 extends parallel to the second inner tapered surface 114*b* of the second flange member 114 and defines a first cutout 113, the first inner tapered surface 114*a* of the second flange member 114 extends parallel to the second inner tapered surface 116*b* of the third flange member 116 and defines a second cutout 115, and the first inner tapered surface 116*a* of the third flange member 116 extends parallel to the second inner tapered surface 112*b* of the first flange member 112 and defines a third cutout 117. Each of the first inner tapered surface 112*a* of the first flange member 112 and the second inner tapered surface 114*b* of the second flange member 114, the first inner tapered surface 114*a* of the second flange member 114 and the second inner tapered surface 116*b* of the third flange member 116, and the first inner tapered surface 116*a* of the third flange member 116 and the second inner tapered surface 112*b* of the first flange member 112 are separated by a distance "D1". The distance "D1" is the same as the diameter "$d_1$" of the semi-cylindrical sections 122*a*, 124*a*, 126*a* of the respective first, second, and third lobe members 122, 124, 126, respectively, of the first lobed portion 120 on the middle shaft 104 of the drive assembly 100.

Figure 8:
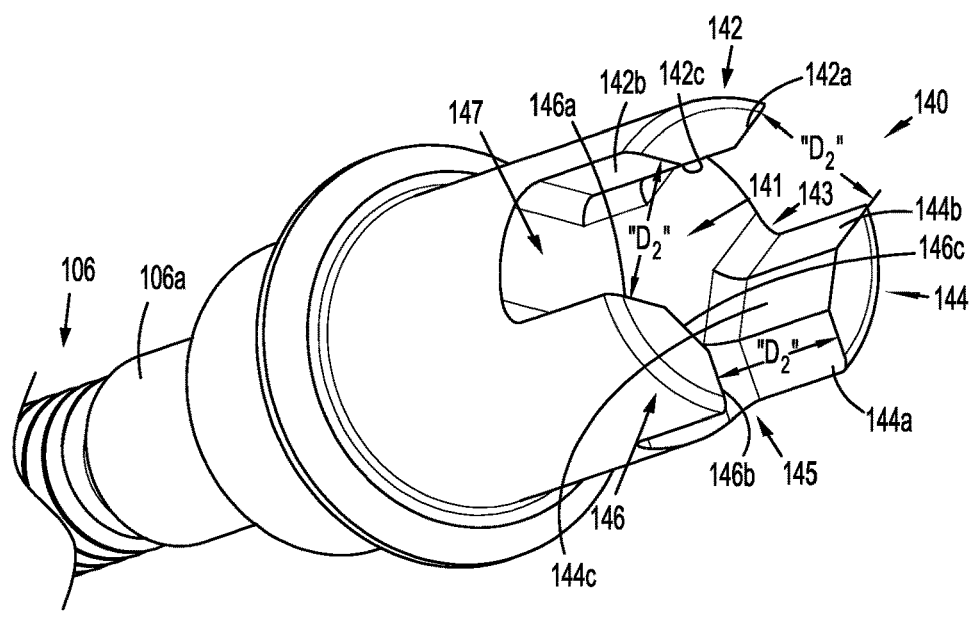
FIG. 8 is an enlarged view of the indicated area of detail shown in FIG. 3.

FIG. 8 illustrates the second castellated portion 140 on the proximal portion 106*a* of the output shaft 106 of the drive assembly 100 (FIG. 2). The second castellated portion 140 is substantially similar to the first castellated portion 110 (FIG. 7) on the distal portion 102*b* of the input shaft 102, including first, second, and third flange members 142, 144, 146 corresponding in number to the number of lobe members of the second lobed portion 130. Each of the first, second, and third flange members 142, 144, 146 includes a first inner tapered surface 142*a*, 144*a*, 146*a*, respectively, a second inner tapered surface 142*b*, 144*b*, 146*b*, respectively, and a planar surface 142*c*, 144*c*, 146*c*, respectively, extending between the respective first inner tapered surfaces 142*a*, 144*a*, 146*a* and the respective second inner tapered surfaces 142*b*, 144*b*, 146*b*. The planar surfaces 142*c*, 144*c*, 146*c* of the respective first, second, and third flange members 142, 144, 146 define a longitudinal recess 141 that is configured to receive the second lobed portion 130 on the middle shaft 104 of the drive assembly 100.

Each of the first inner tapered surfaces 142*a*, 144*a*, 146*a* of the respective first, second, and third flange members 142, 144, 146 forms an angle of one hundred twenty degrees (120°) relative to the respective second inner tapered surfaces 142*b*, 144*b*, 146*b* of the first, second, and third flange members 142, 144, 146. In this manner, the first inner tapered surface 142*a* of the first flange member 142 extends parallel to the second tapered surface 144*b* of the second flange member 144 and defines a first cutout 143, the first inner tapered surface 144*a* of the second flange member 144 extends parallel to the second inner tapered surface 146*b* of the third flange member 146 and defines a second cutout 145, and the first inner tapered surface 146*a* of the third flange member 146 extends parallel to the second inner tapered surface 142*b* of the first flange member 142 and defines the third cutout 117.

Each of the first inner tapered surface 142*a* of the first flange member 142 and the second inner tapered surface 144*b* of the second flange member 144, the first inner tapered surface 144*a* of the second flange member 144 and the second inner tapered surface 146*b* of the third flange member 146, and the first inner tapered surface 146*a* of the third flange member 146 and the second inner tapered surface 142*b* of the first flange member 142 are separated by a distance "D2". The distance "D2" is the same as the diameter "$d_2$" of the semi-cylindrical sections 132*a*, 134*a*, 136*a* of the respective first, second, and third lobe members 132, 134, 136, respectively, of the second lobed portion 130 on the middle shaft 104 of the drive assembly 100 (FIG. 3).

Figures 9, 10:
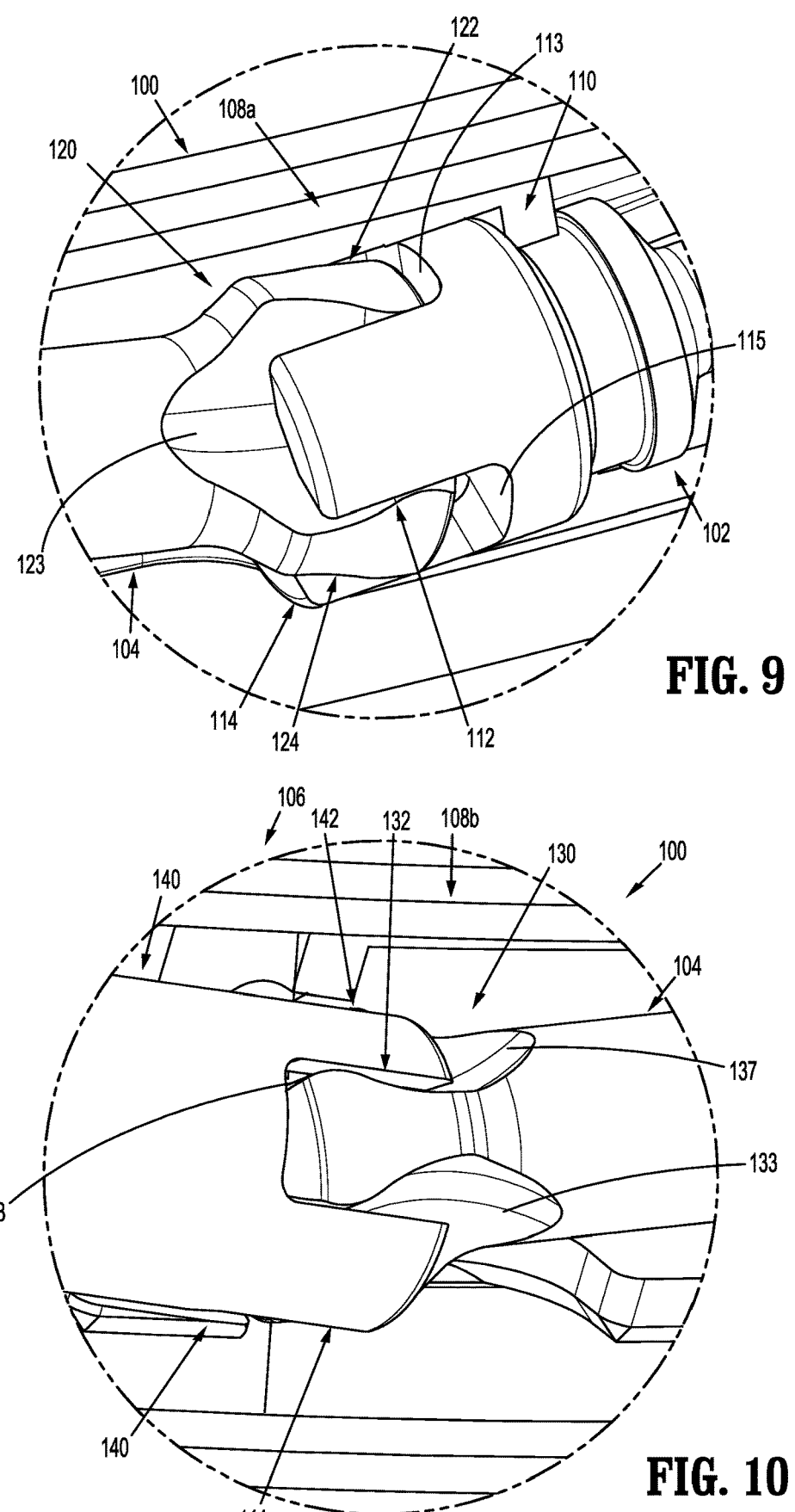
FIG. 9 is an enlarged view of the indicated area of detail shown in FIG. 2.
FIG. 10 is an enlarged view of the indicated area of detail shown in FIG. 2.

FIG. 9 illustrates the first joint 108*a* of the drive assembly 100 including the first lobed portion 120 of the middle shaft 104 of the drive assembly 100 in engagement with the first castellated portion 110 of the input shaft 102 of the drive assembly 100. More particularly, the first lobed portion 120 of the middle shaft 104 is received within the longitudinal recess 111 (FIG. 7) of the first castellated portion 110 of the input shaft 102 such that the first lobe member 122 of the first lobed portion 120 is positioned within the first cutout 113 of the first castellated portion 110, the second lobe member 124 is positioned within the second cutout 115 of the first castellated portion 110, and the third lobe member 126 (FIG. 6) is positioned within the third cutout 117 (FIG. 7) of the first castellated portion 110. The first recess 123 of the first lobed portion 120 accommodates pivotal movement of the first flange member 112 of the first castellated portion 110 relative to the first lobed portion 120, the second recess 125 (FIG. 5) of the first lobed portion 120 accommodates pivotal movement of the second flange member 114 of the first castellated portion 110 relative to the first lobed portion 120, and the third recess 127 (FIG. 6) accommodates pivotal movement of the third flange member 116 (FIG. 7) of the first castellated portion 110 relative to the first lobed portion 120.

FIG. 10 illustrates the second joint 108*b* of the drive assembly 100 including the second lobed portion 130 of the middle shaft 104 in engagement with the second castellated portion 140 of the output shaft 106. More particularly, the second lobed portion 130 of the middle shaft 104 is received within the longitudinal recess 141 (FIG. 8) of the second castellated portion 140 of the output shaft 106 such that the first lobe member 132 of the second lobed portion 130 is positioned within the first cutout 143 of the second castellated portion 140, the second lobe member 134 (FIG. 6) of the second lobed portion 130 is positioned within the second cutout 145 (FIG. 8) of the second castellated portion 140, and the third lobe member 136 (FIG. 6) of the second lobed portion 130 is positioned within the third cutout 147 (FIG. 8) of the second castellated portion 140. The first recess 133 of the second lobed portion 130 accommodates pivotal movement of the second flange member 144 of the second castellated portion 140 relative to the second lobed portion 130, the second recess 135 (FIG. 6) of the second lobed portion 130 accommodates pivotal movement of the third flange member 146 (FIG. 8) of the second castellated portion 140 relative to the second lobed portion 130, and the third recess 137 of the second lobed portion 130 accommodates pivotal movement of the first flange member 146 of the second castellated portion 140 relative to the second lobed portion 130.

Figures 11, 12:
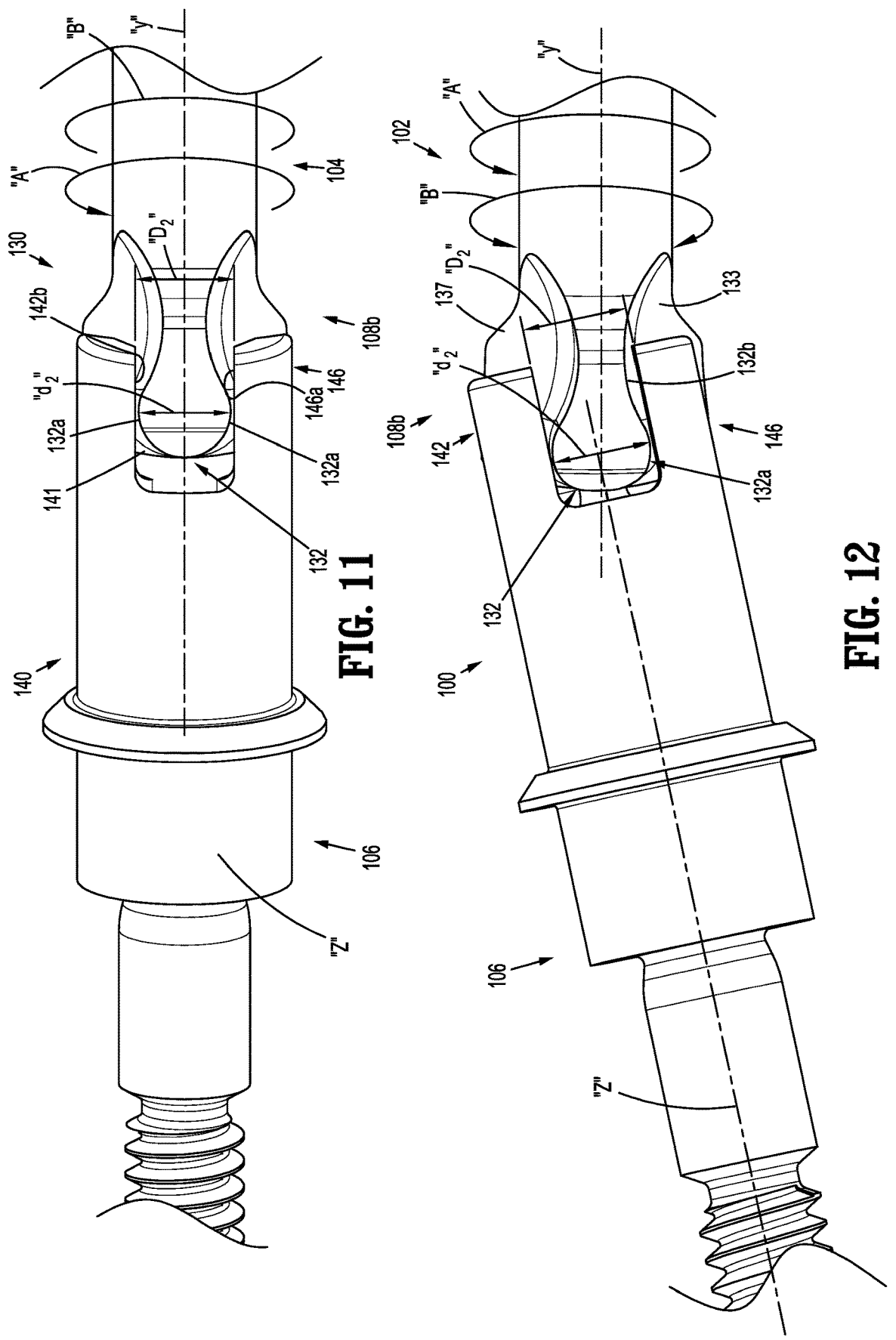
FIG. 11 is a perspective view of a second joint of the drive assembly shown in FIG. 3, with a middle shaft aligned with an output shaft.
FIG. 12 is the perspective view of the second joint of the drive assembly shown in FIG. 3, with the middle shaft at an angle relative to the output shaft.

FIG. 11 illustrates engagement between the second lobed portion 130 of the middle shaft 104 of the drive assembly 100 and the second castellated portion 140 of the output shaft 106 of the drive assembly 100 when the middle shaft 104 and the output shaft 106 are aligned. Although the interaction between the second lobed portion 130 and the second castellated portion 140 will be described in detail with regards to the first lobe member 132 and first and third flange members 142, 146, it is understood that the interaction between the second and third lobe members 134, 136 of the second lobed portion 130 of the middle shaft 104 with the second and third flange members 144, 146 and the second and first flange members 144, 142, respectively, and the first, second, third lobe members 122, 124, 126 of the first lobed portion 120 and the respective first, second, and third flange members 112, 114, 116 of the first castellated portion 110 of the input shaft 102 are the same.

When the second lobed portion 130 on the middle shaft 104 of the drive assembly 100 is received within the longitudinal recess 141 of the second castellated portion 140 of the output shaft 106, the first lobe member 132 is received within the third cutout 147 defined between the first and third flange members 142, 146. As noted above, the semi-cylindrical section 132a of the first lobe member 132 of the second lobed portion 130 includes the diameter "d2". The diameter "d2" is that same as the distance "D2" between the second tapered surface 142b of the first flange member 142 and the first tapered surface 146a of the third flange member 146. In this manner, the semi-cylindrical sections 132a of the first lobe member 132 engage the second tapered surface 142b of the first flange member 142 and the first tapered surface 144a of the third flange member 144, rotationally locking the middle shaft 104 relative to the output shaft 106.

As the middle shaft 104 of the drive assembly 100 is rotated about its longitudinal axis "y" in a first direction, as indicated by arrow "A", engagement between the semi-cylindrical section 132a of the first lobe member 132 of the second lobed portion 130 of the middle shaft 104 and the second tapered surface 142b of the first flange member 142 and the first tapered surface 146a of the third flange member 146 of the output shaft 106 causes the output shaft 106 to be rotated about its longitudinal axis "z" in the same first direction. Conversely, when the middle shaft of the drive assembly 100 is rotated about its longitudinal axis "y" in a second direction, as indicated by arrow "B", engagement between the semi-cylindrical section 132a of the first lobe member 132 of the second lobed portion 130 of the middle shaft 104 and the second tapered surface 142b of the first flange member 142 and the first tapered surface 146a of the third flange member 146 of the output shaft 106 causes the output shaft 106 to be rotated about its longitudinal axis "z" in the same second direction.

FIG. 12 illustrates engagement between the second lobed portion 130 of the middle shaft 104 and the second castellated portion 140 of the output shaft 106 when the output shaft 106 is disposed at an angle relative to the middle shaft 104. When the output shaft 106 is disposed at an angle relative to the middle shaft 104, the semi-cylindrical section 132a of the first lobe member 132 of the first lobed portion 120 of the middle shaft 104 remains engaged with the second tapered surface 142b of the first flange member 142 and the first tapered surface 146a of the third flange member 146 of the output shaft 106. The waist section 132b of the first lobe member 132 of the second lobed portion 130 of the middle shaft 104 and the first and third recess 133, 137 in the second lobed portion 130 accommodate the respective first and third flange member 142, 146 of the second castellated portion 140 of the output shaft 106 when the middle shaft 104 and the output shaft 106 are at an angle relative to each other.

When the output shaft 106 of the drive assembly is at an angle relative to the middle shaft 104 of the drive assembly 100, as the middle shaft 104 is rotated about its longitudinal axis "y", as indicated by arrow "A", the output shaft 106 is rotated about its longitudinal axis "z" in the same first direction. The semi-cylindrical section 132a of the first lobe member 132 of the second lobed portion 130 remains engaged with the first and third flange members 142, 146 of the second castellated portion 140 as the second lobed portion 130 of the middle shaft 104 pivots relative to the second castellated portion 140 as the middle shaft 104 and output shaft 106 rotate about their longitudinal axes "y", "z", respectively, in the first direction. The waist section 132b of the first lobe member 132 of the second lobed portion 130 of the middle shaft 104 and the first and third recess 133, 137 in the second lobed portion 130 accommodate the respective first and third flange members 142, 146 of the second castellated portion 140 of the output shaft 106 as the second lobed portion 130 of the middle shaft 104 pivot relatives relative to second castellated portion 140 of the output shaft 106 as the middle shaft 104 and the output shaft 106 rotate about their respective longitudinal axes "y", "z" in the first direction.

Conversely, when the middle shaft of the drive assembly 100 is rotated about its longitudinal axis "y" in a second direction, as indicated by arrow "B", engagement between the semi-cylindrical section 132a of the first lobe member 132 of the second lobed portion 130 of the middle shaft 104 and the second tapered surface 142b of the first flange member 142 and the first tapered surface 146a of the third flange member 146 of the output shaft 106 causes the output shaft 106 to be rotated about its longitudinal axis "z" in the same second direction. The semi-cylindrical section 132a of the first lobe member 132 of the second lobed portion 130 remains engaged with the first and third flange members 142, 146 of the second castellated portion 140 as the second lobed portion 130 of the middle shaft 104 pivots relative to the second castellated portion 140 as the middle shaft 104 and output shaft 106 rotate about their longitudinal axes "y", "z", respectively, in the second direction. The waist section 132b of the first lobe member 132 of the second lobed portion 130 of the middle shaft 104 and the first and third recess 133, 137 in the second lobed portion 130 accommodate the respective first and third flange member 142, 146 of the second castellated portion 140 of the output shaft 106 as the second lobed portion 130 of the middle shaft 104 pivot relatives relative to second castellated portion 140 of the output shaft 106 as the middle shaft 104 and the output shaft 106 rotate about their respective longitudinal axes "y", "z", in the second direction.

As noted above, a distal end of the output shaft 106 may include a screw member 106b (FIG. 2) or may otherwise be connected to the trocar assembly 30 (FIG. 2). Rotation of the output shaft 106 in a first direction about its longitudinal axis "z" advances the trocar member 32 (FIG. 2) of the trocar assembly 30 relative to the adapter assembly 14 (FIG. 1). Conversely, rotation of the output shaft 106 in a first direction about its longitudinal axis "z" retracts the trocar member 32 of the trocar assembly 30 relative to the adapter assembly 14.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

The invention claimed is:

1. A drive assembly for an adapter assembly of a surgical device, the drive assembly comprising:

an input shaft having a distal portion including a first castellated portion;

a middle shaft having a proximal portion and a distal portion, the proximal portion of the middle shaft including a first lobed portion in operable engagement with the first castellated portion of the input shaft, the distal portion of the middle shaft including a second lobed portion, wherein the first lobed portion and the second lobed portion each include three lobe members; and an output shaft having a proximal portion and a distal portion, the proximal portion of the output shaft including a second castellated portion in operable engagement with the second lobed portion.

2. The drive assembly of claim 1, wherein the first castellated portion and the second castellated portion each include three flange members.

3. The drive assembly of claim 2, wherein the first castellated portion and the second castellated portion define three cutouts.

4. The drive assembly of claim 3, wherein the cutouts of the first castellated portion correspond in number to the number of three lobe members of the first lobed portion, and the cutouts of the second castellated portion correspond in number to the number of lobe members of the second lobed portion.

5. The drive assembly of claim 4, wherein each lobe member of the three lobe members of the first and second lobed portions includes a semi-cylindrical portion and a waist portion.

6. The drive assembly of claim 5, wherein each of the first lobed portion and the second lobed portion define three recesses.

7. The drive assembly of claim 6, wherein the waist portions and the three recesses of the three lobe members of the first lobed portion accommodate pivoting of the middle shaft relative to the input shaft.

8. The drive assembly of claim 6, wherein the waist portion and the three recesses of the three lobe members of the second lobed portion accommodate pivoting of the output shaft relative to the middle shaft.

9. The drive assembly of claim 1, wherein the distal portion of the output shaft includes a drive screw.

10. An adapter assembly for connecting a handle assembly to an end effector, the adapter assembly comprising:

a coupling assembly configured for operable connection with a handle assembly;

a straight portion secured to the coupling assembly;

a curved portion extending from the straight portion; and a drive assembly extending from the handle assembly through the curved portion, the drive assembly including:

an input shaft having a distal portion including a first castellated portion;

a middle shaft having a proximal portion and a distal portion, the proximal portion of the middle shaft including a first lobed portion in operable engagement with the first castellated portion of the input shaft, the distal portion of the middle shaft including a second lobed portion, wherein the first lobed portion and the second lobed portion of the drive assembly each include three lobe members; and an output shaft having a proximal portion and a distal portion, the proximal portion of the output shaft including a second castellated portion in operable engagement with the second lobed portion.

11. The adapter assembly of claim 10, wherein the first castellated portion and the second castellated portion each include three flange members.

12. The adapter assembly of claim 11, wherein the first castellated portion and the second castellated portion include three cutouts.

13. The adapter assembly of claim 12, wherein the cutouts of the first castellated portion correspond in number to the number of lobe members of the first lobed portion, and the cutouts of the second castellated portion correspond in number to the number of lobe members of the second lobed portion.

14. The adapter assembly of claim 13, wherein each lobe member of the three lobe members of the first and second lobed portions includes a semi-cylindrical portion and a waist portion.

15. The adapter assembly of claim 14, wherein each of the first lobed portion and the second lobed portion define three recesses.

16. The adapter assembly of claim 15, wherein the waist portions of the three lobe members of the first lobed portion and the three recesses of the first lobed portion accommodate pivoting of the middle shaft relative to the input shaft.

17. The adapter assembly of claim 15, wherein the waist portion of the three lobe members of the second lobed portion and the three recesses of the second lobed portion accommodate pivoting of the output shaft relative to the middle shaft.

18. A surgical device comprising:

a handle assembly;

an adapter assembly secured to the handle assembly;

an end effector secured to the adapter assembly; and a drive assembly extending from the handle assembly and positioned within the adapter assembly, the drive assembly including:

an input shaft having a distal portion including a first castellated portion;

a middle shaft having a proximal portion and a distal portion, the proximal portion of the middle shaft including a first lobed portion in operable engagement with the first castellated portion of the input shaft, the distal portion of the middle shaft including a second lobed portion, wherein the first lobed portion and the second lobed portion of the drive assembly each include three lobe members; and an output shaft having a proximal portion and a distal portion, the proximal portion of the output shaft including a second castellated portion in operable engagement with the second lobed portion.

*   *   *   *   *